US012708273B2

(12) United States Patent
Jain et al.

(10) Patent No.: US 12,708,273 B2
(45) Date of Patent: Aug. 18, 2026

(54) SYSTEM AND METHOD OF MEASURING AND ESTIMATING HUMAN HEALTH PARAMETERS

(71) Applicant: TATA INDUSTRIES LIMITED, Fort Mumbai Maharashtra (IN)

(72) Inventors: Abhishek Jain, Maharashtra (IN); Govinda Gupta, Maharashtra (IN); Teja Vardhan, Maharashtra (IN)

( * ) Notice: Subject to any disclaimer, the term of this patent is extended or adjusted under 35 U.S.C. 154(b) by 211 days.

(21) Appl. No.: 18/281,555

(22) PCT Filed: Mar. 11, 2022

(86) PCT No.: PCT/IN2022/050228

§ 371 (c)(1),
(2) Date: Sep. 11, 2023

(87) PCT Pub. No.: WO2022/190134

PCT Pub. Date: Sep. 15, 2022

(65) Prior Publication Data

US 2024/0148258 A1 May 9, 2024

(30) Foreign Application Priority Data

Mar. 12, 2021 (IN) ............................ 202121010520

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0022* (2013.01); *A61B 5/7267* (2013.01);
(Continued)

(58) Field of Classification Search
CPC ... A61B 5/0205; A61B 5/0022; A61B 5/7267; A61B 5/01; A61B 5/022; A61B 5/02405; A61B 5/02416; A61B 5/14551; A61B 5/02055; A61B 2560/0233; A61B 2560/0238; A61B 7/045; G16H 40/40; G16H 40/67; G16H 40/63; G16H 50/30
See application file for complete search history.

(56) References Cited

U.S. PATENT DOCUMENTS 8,968,196 B2 * 3/2015 Teller .................... A61B 5/398
600/301
2017/0367599 A1 * 12/2017 Sanyal ................ A61B 5/0024

FOREIGN PATENT DOCUMENTS

KR 20200034329 A * 3/2020 .......... A61B 5/7292

* cited by examiner

*Primary Examiner* — Carl H Layno
*Assistant Examiner* — Maria Catherine Anthony

(57) ABSTRACT

The present invention relates to a system and a method for measuring health parameter of a user. The system comprises two or more sensing modules for capturing values of two or more sensed measurements associated with health of the user. The two or more sensing modules are communicatively coupled with a processor configured to determine a value of the health parameter by processing the values of the two or more sensed measurements. The value of the health parameter is determined based on a weighted measurement of the values of the two or more sensed measurements. An output of one sensing module of the two or more sensing modules is used to calibrate another sensing module of the two or more sensing modules.

20 Claims, 3 Drawing Sheets

(51) Int. Cl.
*G16H 40/40* (2018.01)
*G16H 40/67* (2018.01)

(52) U.S. Cl.
CPC ............. *G16H 40/40* (2018.01); *G16H 40/67* (2018.01); *A61B 2560/0223* (2013.01)

SYSTEM AND METHOD OF MEASURING AND ESTIMATING HUMAN HEALTH PARAMETERS

FIELD OF THE INVENTION

The present invention in general relates to techniques that enable usage of multiple sensing modules for improving accuracy of measurement and allow for measurement of unique parameters that cannot be measured by one sensing module alone.

BACKGROUND OF THE INVENTION

Advancements in certain technologies over the last decade have allowed for introduction of certain sensing modules in wearable devices that allow users to continuously monitor certain health related parameters. For example, several wearable smartwatches allow users to measure heart rate in a non-intrusive manner. However, in many cases, this ease of use comes at a cost of accuracy. Lack of accurate data prevents users and their respective physicians from deriving meaningful insights into the well-being of the users. Devices that are accurate are often not as easy to use and are difficult to integrate into the lifestyle of a user.

Therefore, there is a motivation to develop innovative solutions that allow users to measure or estimate their healthcare or wellness parameters in a very easy to use manner, without compromising on accuracy of the measurement. While some emerging technologies show the promise of ease of use and accurate measurements or estimations, it is likely that such technologies will take several years before being validated and found fit for use for measuring or estimating health parameters accurately for humans.

In recent years, sensor fusion has been used successfully to achieve additional and/or more accurate insights into user wellbeing. Sensor fusion leverages inputs from more than one sensing module to measure or estimate one or more parameters. For example, by leveraging data from ElectroCardioGram (ECG) and PhotoPlethysmoGraphy (PPG) sensing module, it is possible to estimate Pulse Arrival Time (PAT) and Pulse Transit Time (PTT). Further, there are certain sensing modules that can provide additional insights into a user's wellbeing, but only if calibrated well and sometime, at frequent time intervals. For example, research has indicated that data from PPG sensing modules can be used to estimate Blood Pressure (BP) but only with initial calibration, followed by periodic calibration, using BP measurement obtained from conventional or higher accuracy BP measurement devices such as the ones using auscultatory or oscillometric approaches.

However, such requirements that call for obtaining inputs from different sensing modules or measurement apparatuses when the sensing modules or measurement apparatuses are hosted on two physically different and separate devices can significantly diminish the ease of use for a user. This can, in turn, lead to decreased usage of the devices, which in turn leads to fewer data points being collected about the user's wellbeing. Therefore, a method and a system that allows user to leverage outputs from multiple sensing modules in an easy manner is needed.

OBJECTIVE OF THE INVENTION

A primary objective of present disclosure is to provide a method and a system that either enables more than one sensing module to be housed in one physical device or be housed in two separate physical devices but be communicatively coupled to one processor. Further, the method and the system enables such, more than one sensing module, to be easy to use and also allows for measurement and/or estimation of health parameters that need, or can benefit from, inputs from more than one sensing module.

Another objective of present disclosure is to provide a method and a system that enables users to use more than one sensing module in a manner that is easy to use and also allows for measurement and/or estimation of health parameters that need inputs from more than one sensing module.

Another objective of present disclosure is to provide a method and a system that enables users to use more than one sensing module in a manner that is easy to use and also allows for calibration of one sensing module using data output from another sensing module.

Yet another objective of present disclosure is to provide a method and a system for determining performance of a first sensing module based on comparison of measurement data obtained from the first sensing module to measurement data obtained from a second sensing module.

Another objective of present disclosure is to provide a method and a system that notifies a user to perform certain task that generates measurement data from one sensing module, such that the measurement data is used by a processor to measure certain parameter in conjunction with measurement data obtained from a second sensing module or to generate calibration information for the second sensing module.

SUMMARY OF THE INVENTION

Before the present methods, systems, and hardware enablement are described, it is to be understood that this invention in not limited to the particular systems, and methodologies described, as there can be multiple possible embodiments of the present invention which are not explicitly illustrated in the present disclosure. It is also to be understood that the terminology used in the description is for the purpose of describing the particular versions or embodiments only and is not intended to limit the scope of the present invention which will be limited only by the appended claims.

The present invention relates to a system and a method for measurement of health parameter of a user. The system may comprise two or more sensing modules for capturing values of two or more sensed measurements associated with health of a user. The system may also comprise a processor configured to determine a value of the health parameter by processing the values of the two or more sensed measurements captured from the two or more sensing modules.

In one aspect, weightages may be assigned to the values of the two or more sensed measurements captured by the two or more sensing modules. The weightages may be predefined and depend on reliability of the two or more sensed measurements captured by the two or more sensing modules or contextual parameters. Alternatively, the weightages may be continuously updated through a self-learning process.

In one aspect, the value of the health parameter may be determined as a weighted average of the values of the two or more sensed measurements.

In one aspect, an output of one sensing module of the two or more sensing modules may be used to calibrate another sensing module of the two or more sensing modules.

In one aspect, the two or more sensing modules may include Photoplethysmography (PPG) sensing modules, cuff-based blood pressure sensing modules, cuff-less blood pressure sensing modules, digital auscultation sensing modules, Electrocardiography (ECG) sensing modules, Infrared thermometers, or Complementary Metal Oxide Semiconductor (CMOS) based sensing modules.

In one aspect, each sensing module of the two or more sensing modules may capture values of more than one sensed measurement.

In one aspect, the processor may be communicatively coupled to a notification means for notifying a user about the value of the health parameter, requirement of calibration of the two or more sensing modules, or availability of at least one of the two or more sensing modules.

In one aspect, the system may be connected with a user device via a wireless communication module, to communicate the value of the health parameter.

In one aspect, the user device may allow communication of the system with a cloud based server for communicating the two or more sensed measurements and the final value of the health parameter.

In one aspect, the system includes a memory for storing information related to identification of the two or more sensing modules useable for capturing values of two or more sensed measurements, determining calibration data of the two or more sensing modules for a plurality of users, or determining availability of the two or more sensing modules.

In one implementation, a method for measuring health parameters may comprise determining, by a processor, availability of two or more sensing modules required to capture two or more sensed measurements associated with a user. The values of the parameter may be captured by the two or more sensing modules. The values of the two or more sensed measurements may be processed by the processor to obtain a value of a health parameter of the user.

In one aspect, the value of the health parameter may be determined by assigning weightages to the values of the two or more sensed measurements captured by the two or more sensing modules, and determining weighted average of the values of the two or more sensed measurements. The weightages may be predefined and depend on reliability of measurement of the two or more sensed measurements captured by the two or more sensing modules. Alternatively, the weightages may be continuously updated through a self-learning process.

In one aspect, an output of one sensing module of the two or more sensing modules may be utilized to calibrate another sensing module of the two or more sensing modules.

In one aspect, calibration may be performed based on one or more of absence of calibration data for the user, lapse of a predetermined period of time since calibration data for the user was obtained, and deviation of the value of the health parameter from an expected value of the health parameter.

In one aspect, the two or more sensed measurements obtained from the two or more sensing modules may be synchronized for obtaining another sensed measurement.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings.

DETAILED DESCRIPTION OF THE INVENTION

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described.

The disclosed embodiments are merely exemplary of the invention, which may be embodied in various forms. Accordingly, the sensing modules and health parameters used to describe the invention are not restrictive and the invention may be used in embodiments that use sensing modules other than the ones that are mentioned in the description. The invention may benefit non-healthcare related embodiments such as industrial, automotive etc.

Figure 1:
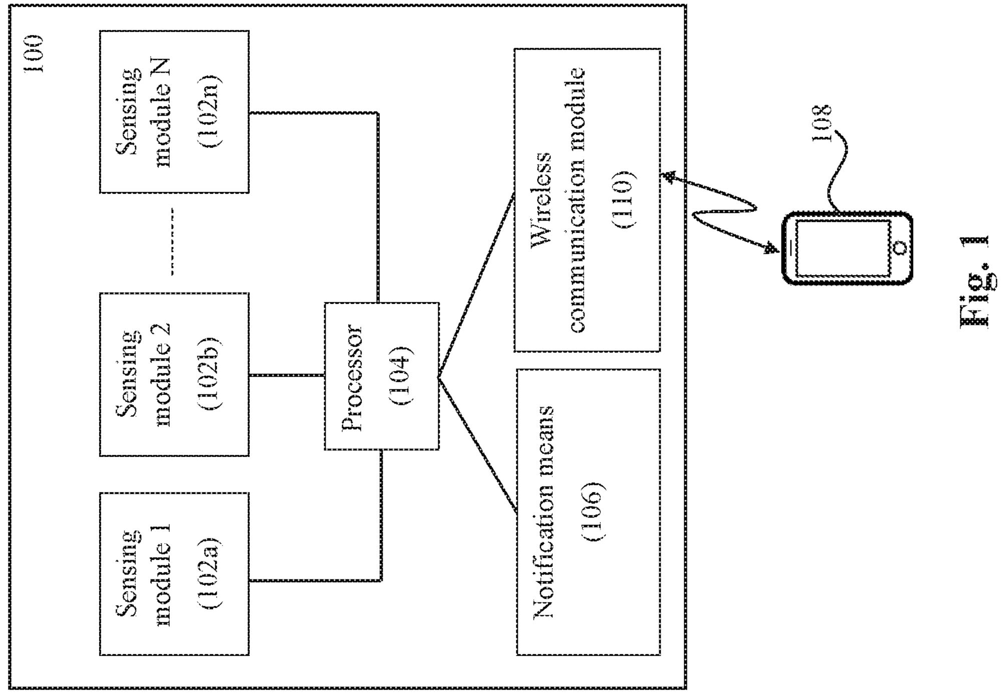
FIG. 1 is a block diagram representing a system including multiple sensing modules for measuring multiple sensed measurements, in accordance with an embodiment of present disclosure.

FIG. 1 illustrates a block diagram of a system 100 including multiple sensing modules (alternatively referred as sensors) 102*a* through 102*n* (hereinafter labelled as 102) for capturing one or more sensed measurements. The one or more sensed measurements may be associated with health of a user. The two or more sensed measurements may be synchronized for obtaining another sensed measurement. The sensing modules 102 are communicatively coupled to a processor 104 via a wired or wireless communication link. The wireless communication link could utilize any of the wireless communication protocols including, but not limited to, Bluetooth, Infrared, Wireless Application Protocol (WAP) or any customized protocol(s). The processor 104 is able to receive outputs from the sensing modules 102. The processor 104 is programmed to process the one or more sensed measurements to estimate a health parameter. For example, heart rate variability of the user may be determined based on values captured an ECG sensor and a PPG sensor. The processor 104 also performs generating calibrating information, for example generating calibrating information for a first sensing module 102*a* based on an output of a second sensing module 102*b*. It is also possible that certain sensing modules can include a separate processing unit that can perform measurement of certain health parameters at the sensing module level itself, in which case the processor can be configured to receive data corresponding to the measured parameters from such sensing module.

Each of the sensing modules 102 may be configured to be always present in communicative coupling with the processor 104 or may be configured to be communicatively coupled to the processor 104 on demand by means of the wired or wireless link. It may be noted that in some cases while a part of a particular sensing module, for example the sensing module 102*a*, may be present in communicative coupling with the processor 104, one or more sub-components of the sensing module 102*a* may need to be attached to complete the sensing module 102*a* and enable it to perform a measurement. For example, in case of a cuff-based blood pressure monitoring device, all the components except the cuff may be communicatively coupled to a processor all times. However, the cuff might be detachable and could be connected when needed. It should be noted that the processor 104 can be configured to gather information about the availability of the sensing modules 102, in part or in full. For example, the system 100 may include additional sensing modules or internal communication protocols that allow the sensing modules 102 to report their respective availability, or availability of a respective sub-component. In one implementation, the system 100 may include an additional sensing module that enables the system 100 to determine if an inflatable cuff is attached or not. It should also be noted that the additional sensing module can also be configured to determine presence or absence of a sub-component by analyzing data generated by the additional sensing module. For example, the blood pressure monitoring device might determine that the cuff is not attached if a pressure sensing module fails to observe any increase in pressure after pumping of air for a predetermined number of seconds by an air pump.

The processor 104 may also be communicatively coupled to a notification means 106 for notifying one or more users. The notification means 106 could include a display connected to the processor 104 through a wired or a wireless link. Further, the processor 104 may be connected to a user device 108 via a wireless communication module 110. The user device 108 may be a desktop, laptop, mobile phone or any other handheld smart device. Wireless connection between the user device 108 and the wireless communication module 110 could be enabled through a suitable wireless communication protocol. Further, the processor 104 may also communicate to a cloud server through the user device 108.

Figure 2:
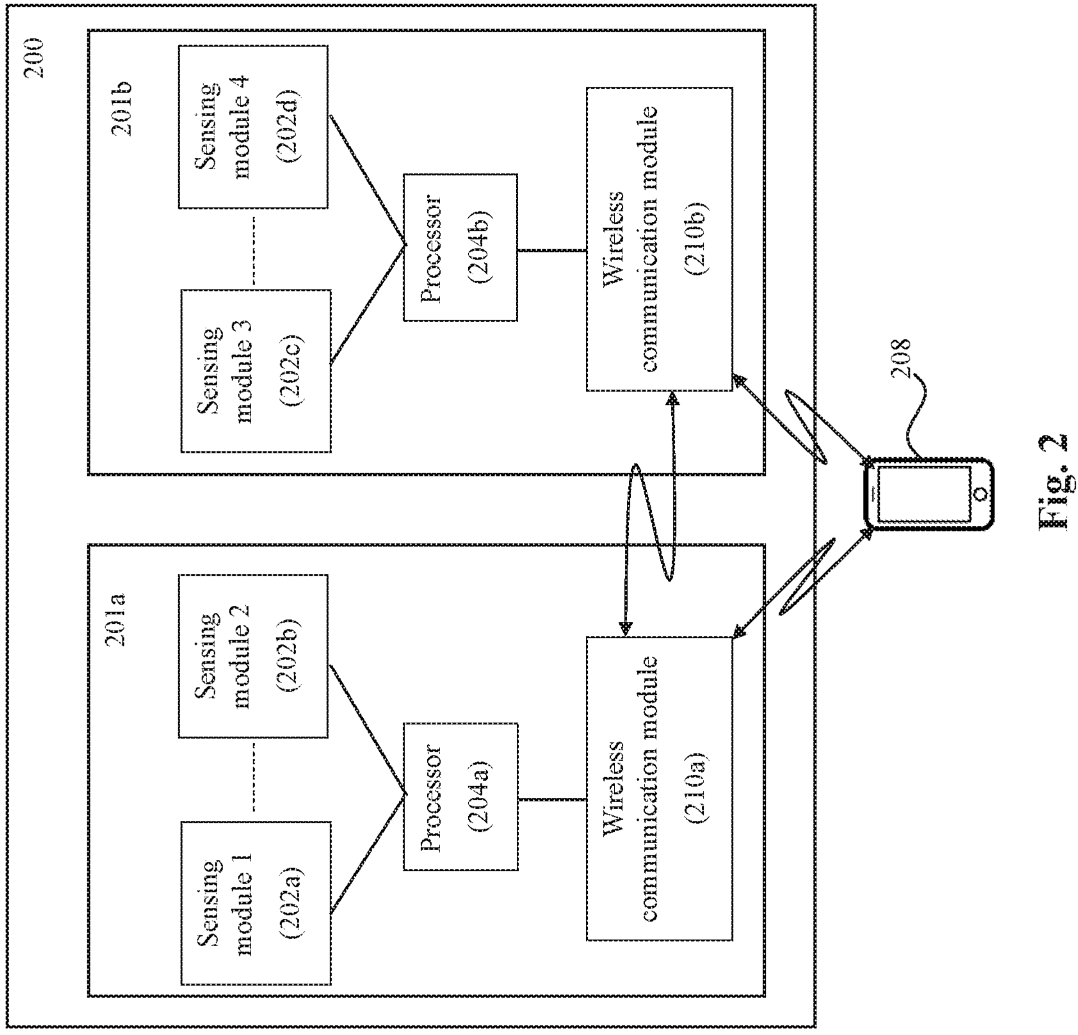
FIG. 2 illustrates a block diagram representing usage of multiple systems having multiple sensing modules, in accordance with an embodiment of present disclosure.

FIG. 2 illustrates a block diagram representing usage of multiple systems 201*a* and 201*b* (collectively referred as 200) having multiple sensing modules. Each of the systems 201*a* and 201*b* may include multiple sensing modules i.e. the system 201*a* includes a sensing module 1 202*a* and a sensing module 2 202*b* and the system 201*b* includes a sensing module 3 202*c* and a sensing module 4 202*d*. Within the system 201*a*, the sensing module 1 202*a* and the sensing module 2 202*b* are connected to a processor 204*a* which is connected with a wireless communication module 210*a*. Within the system 201*b*, the sensing module 3 202*c* and the sensing module 4 202*d* are connected to a processor 204*b* which is connected with a wireless communication module 210*b*. The processor 204*a* and the processor 204*b* are communicatively coupled with each other via their respective wireless communication modules 210*a* and 210*b*. Wireless link between the wireless communication modules 210*a* and 210*b* could utilize any one of the wireless communication protocols including Bluetooth, Infrared, Wireless Application Protocol (WAP) or any customized protocol.

Each of the processors 204*a* and 204*b* are able to receive outputs from their respective sensing modules and to perform one or more of, measuring a parameter, estimating a parameter and generating calibrating information for a particular sensing module using an output of another sensing module. The processors 204*a* and 204*b* may also be communicatively coupled to respective notification means (not illustrated) using a wired or a wireless link. The notification means could include a display for notifying one or more users. Further, the processors 204*a* and 204*b* may be connected to a user device 208 via respective wireless communication modules 210*a* and 210*b*. The user device 208 may be a desktop, laptop, mobile phone or any other handheld smart device. Wireless connection between the user device 208 and the wireless communication modules 110*a* and 210*b* could be enabled through a suitable wireless communication protocol. Further, the processors 204*a* and 204*b* may also communicate to a cloud based platform through the user device 208. The cloud based platform may be utilized to store data related to the values of the sensed measurements captured by the sensing modules 102 and the value of the health parameter.

In one embodiment, a processor of the system 100, 201*a*, or 201*b* might determine that a first sensing module communicatively coupled to the processor needs to be calibrated. In one scenario, the requirement of calibrating the first sensing module may arise after lapse of a predetermined period of time from a previous calibration or on a determination by the processor using other criteria. Based on stored information available to the processor, the processor might further determine that a second sensing module communicatively coupled to the processor is capable of performing a measurement and can provide the processor with information for calibrating the first sensing module. On such determination, the processor is configured to generate a notification or an alert for a user to perform the calibration measurement using the second sensing module. The processor receives the output of the second sensing module and uses it to generate calibration information for the first sensing module and stores it in a memory coupled to the processor.

The sensing modules described in the disclosure could be any type of sensing modules that either alone or in combination with multiple subsystems are capable of providing one or more sensed measurements for determining health parameters. In an embodiment, the sensing modules may be capable of capturing parameters related to human health. In one or more implementations, the sensing modules may include Photoplethysmography sensing modules, cuff-based blood pressure sensing modules, cuff-less blood pressure sensing modules, digital auscultation sensing modules, ECG sensing modules, Infrared thermometers, or Complementary Metal Oxide Semiconductor (CMOS) based sensing modules. It should be noted that this list of sensing modules is just exemplary and not restrictive in any manner. A sensing module, as described above in one or more embodiments, could include multiple components that in combination are able to measure or estimate a particular parameter. For example, a cuff-based blood pressure sensing module may comprise one or more of a cuff, a pump, a valve, a driver, a microprocessor or microcontroller, power management apparatus, Analog to Digital Converter (ADC) component, and a display.

In an embodiment, the processor of the system 100, 201*a*, or 201*b* could be communicatively coupled to one or more sensing modules physically present on the system 100, 201*a*, or 201*b*. The processor may receive the output of the one or more sensing modules to calculate or estimate one or more health parameters of the user. The processor may be configured to determine that a sensing module needed to capture a particular sensed measurement is not present in the system 100, 201*a*, or 201*b*. In one scenario, the processor based on the determination that all the sensing modules needed to capture values of the particular sensed measurement are available, might initiate capturing of values of the sensed measurements using the corresponding sensing modules. In another implementation, the processor based on the determination that one or more sensing modules needed to capture the values of the particular sensed measurements are not available, or a sub-component of such a sensing module is not available, may inform the user about unavailability of a particular sensing module or a sub-component of a sensing-module. Further, the processor may be configured to proceed with the sensed measurements if the unavailable sensing module or the unavailable sub-component of the sensing module are made available i.e. externally connected to the system 100, 201*a*, or 201*b*, using a wired or a wireless communication link. The processor may also be configured to allow the user to change the parameters that the user wants to capture during unavailability of a particular sensing module or a sub-component of a sensing-module.

In another embodiment, the processor of the system 100, 201*a*, or 201*b* might have access to information stored in a memory coupled to the processor. The memory may contain a list of sensing modules that are communicatively coupled to the processor or are available to be communicatively coupled to the processor. The list of sensing module may also contain information regarding sensing modules that may not be communicatively coupled to the processor but can be connected using a wired or a wireless communication link. The memory may further store information for enabling the processor to determine one or more of the below mentioned functions:

i) which one or more sensing modules can be used, either alone or in combination to capture values of one or more sensed measurements, ii) which sensing module requires calibration information to be generated from measurement data of another sensing module, iii) calibration data corresponding to each user that is using the system 100, 201*a*, or 201*b*, if user specific calibration is needed for a sensing module to capture one or more sensed measurements, and iv) which sensing module's performance can be ascertained by cross referencing a part or whole of measurement data of a sensing module with a part or whole of measurement data of another sensing module.

In an embodiment, the system 100, 201*a*, or 201*b* may be a multi-parameter system capable of measuring more than one parameter. The system 100, 201*a*, or 201*b* could include a processor and a first sensing module, a second sensing module, and a third sensing module. The processor can be communicatively coupled with all the sensing modules. The processor may be configured to receive a request from a user of the system 100, 201*a*, or 201*b* to perform measurement of one or more parameters. On receiving the request from the user, the processor could identify the sensing modules required for measuring each of the one or more parameters for the user. The processor could identify the sensing modules based on the information stored in a memory coupled to the processor. The processor could also determine that for a particular parameter measurement, inputs from more than one sensing module are needed. The processor may be configured to received measurement data from the one or more sensing modules, and perform additional computation to derive the parameters that the user requires to measure.

In an embodiment, the system 100, 201*a*, or 201*b* may be a multi-parameter and a multi-user system capable of measuring more than one parameter and is configured to allow more than one users to use the system 100, 201*a*, or 201*b* to perform parameter measurements. The system 100, 201*a*, or 201*b* could include a processor and a first sensing module, a second sensing module, and a third sensing module. The processor may be communicatively coupled with each of the sensing modules. The processor may be configured to determine if the first sensing module needs to obtain initial calibration data or update existing calibration data for a user using measurement data from the second sensing module. The processor may determine such a requirement for calibration based on one or more of absence of calibration information for the user, lapse of a predetermined period of time since the last calibration information for the user was obtained and/or determination that the measurement data from the first sensing module is deviating from expected measurement data for the first sensing module. For example, the deviation between measured data and the expected measurement data can be calculated by determining the expected measurement data from one or more other sensors. It should be noted that the measurement data from the first sensor can correspond to more than one health parameter. For example, a PPG sensor output can be used to estimate Blood Oxygen levels and heart rate. On determining a need for calibration, the processor may be configured to send a notification to the user using one or more medium of sharing such notification. The processor may also be configured to notify the user for the need of calibration when the user tries to measure the parameter next time.

In an embodiment, the system 100, 201*a*, or 201*b* may be a multi-parameter and a multi-user system capable of measuring more than one parameter and configured to allow more than one user to use the system 100, 201*a*, or 201*b* to perform parameter measurements. The system 100, 201*a*, or 201*b* may include a processor and have a first sensing module, a second sensing module, and a third sensing module. The processor may be communicatively coupled with each of the sensing modules. The processor may be configured to determine if the first sensing module needs to obtain initial calibration data or update existing calibration data for a first user using the measurement data from the second sensing module. The processor may obtain the measurement data from the second sensing module as the user performs the measurement and analyzes such measurements to obtain required calibration information for the first sensing module. The processor may be further configured to store the calibration information in a memory coupled to the processor. It should be noted that the system 100, 201*a*, or 201*b* being a multi-user system could require separate calibrations for each user. The processor will therefore perform such calibration tasks for each user, as suggested in present embodiment.

In another embodiment, the system 100, 201*a*, or 201*b* may be a multi-parameter and/or a multi-user system capable of measuring a parameter using data received from two or more sensing modules. A user of the system 100, 201*a*, or 201*b* might select an option to measure a health parameter. The processor of the system 100, 201*a*, or 201*b* may be enabled to check from a database stored into a memory coupled to the processor as to which sensing modules are required to capture values of sensed measurements required to determine a health parameter of a user. The processor may further be enabled to determine the status of each of the required sensing modules. Further, the processor may be enabled to notify the user about lack of availability of one or more required sensing modules. The processor may also be enabled to determine if a sub-component of a sensing module is unavailable. If the processor determines that all the sensing modules needed to perform the measurement are available, the processor may initiate recording using the two or more sensing modules. It may be noted that for measuring certain parameter, the two or more sensing modules may need to operate together i.e. in synchronization. For example, to measure Pulse Arrival Time, the processor may be configured to measure the ECG waveform and PPG waveform in a synchronized manner using respective sensing modules simultaneously. In another example, a digital auscultation device may be used in conjunction with a cuff-based blood pressure measurement sensing module to determine when the Korotkoff sounds are observed which in turn enables determination of the systolic and diastolic blood pressure of the user.

In another embodiment, the system 100, 201*a*, or 201*b* may be a multi-parameter and/or a multi-user system capable of measuring a parameter by using data received from two or more sensing modules. A user of the device might select an option to measure the health parameter. A processor of the system 100, 201*a*, or 201*b* may be enabled to check from a database stored into a memory coupled to the processor as to which sensing modules are required to perform measurement of the health parameter. The database may further contain information about multiple sets of sensing modules that can allow capturing of multiple sensed measurements. For example, Heart rate of a user can be measured using ECG sensing module as well as PPG sensing module. Also, blood pressure of a user can be measured using a cuff-based oscillometric blood pressure measurement device alone, or a PPG based chipset deploying a computation based or neural network based approach but only after being calibrated for each user, using another blood pressure measurement setup, or a combination of a cuff-based blood pressure measurement devices that uses a synchronized digital auscultation device capable of identifying Korotkoff sounds. Further, the database may also be configured to store the accuracy and reliability levels of sensed measurements captured by each of the multiple sets of sensing modules that allows measurement of the health parameter. The processor may further be enabled to determine the status of each of the required sensing modules. Based on the determination that a set of sensing modules are available and another set of sensing modules are unavailable, the processor may further be enabled to provide the user with options of the parameter which could be measured using the available sensing modules. The processor may further be configured to also notify the user about accuracy and reliability levels of the measurements.

Figure 3:
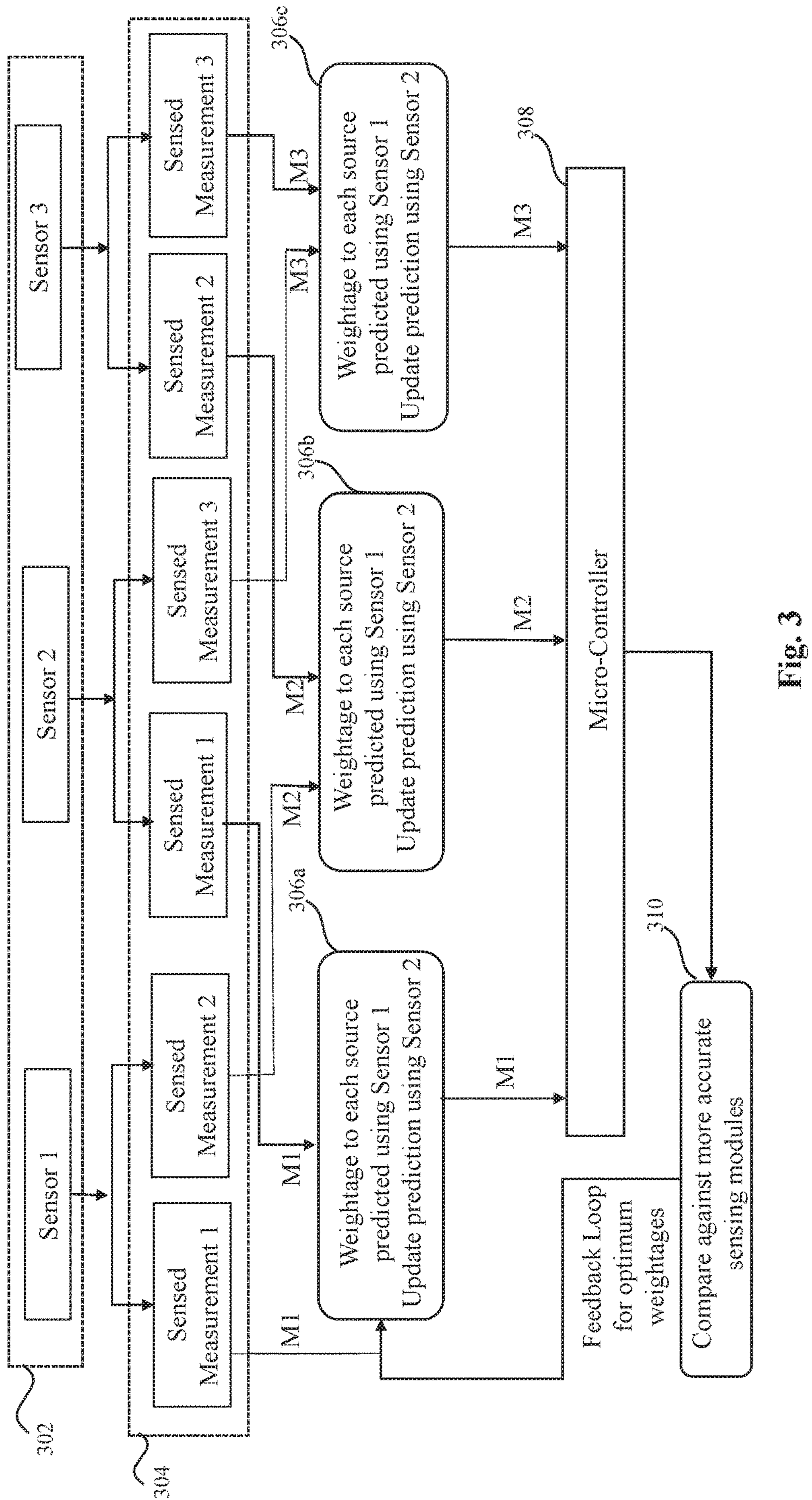
FIG. 3 illustrates a block diagram of a process for determining a health parameter associated with a user, in accordance with an embodiment of present disclosure.

FIG. 3 illustrates a block diagram of a process for determining a health parameter associated with a user. At block 302, multiple sensors, such as sensor 1, sensor 2, and sensor 3 may be used to capture values of two or more sensed measurements associated with the user. The sensors may capture and provide the values of two or more sensed measurements, at block 304. As illustrated in FIG. 3, the sensor 1 provides values of sensed measurement 1 and sensed measurement 2. The sensor 2 provides values of the sensed measurement 1 and sensed measurement 3. The sensor 3 provides values of the sensed measurement 2 and the sensed measurement 3. Successively, values of same sensed measurements determined using different sensors are collated and weightages are assigned to the sensed measurements captured by at least one sensor. In one implementation, the weightages may be predefined by an operator or predefined through mathematical computations, based on certain observations, such as performance and reliability of the sensors. A processor of a system performing the measurement may compute the weightages or allow an operator to set the weightages. Such weightages may then be stored in a database or in a memory of the system. The weightages may be retrieved based on certain reliability of the sensed measurements or contextual parameters, such as time of the day. For example, the database may store different set of weightages for scenarios where the user has weight management issues, if the system determines that there might be motion artefacts present during the measurement or based on the time of the day a sensed measurement was captured.

In certain implementations, the weightages may be updated based on a self-learning process. The self-learning process may be implemented on the cloud server storing values of the sensed measurements and the value of the health parameter, over a time period. The self-learning process may utilize supervised machine learning techniques such as linear classifiers, support vector machines (SVM), decision trees, k-nearest neighbor, random forest, and/or regression algorithms. The supervised machine learning techniques may be used to train data models on the user data i.e. the values of the sensed measurements and the value of the health parameter. Such data models may be then be utilized to update the weightages.

At block 306*a*, values of the sensed measurement 1 captured by the sensor 1 and the sensor 2 are collated, and a weightage may be assigned to the value of the sensed measurement 1 captured by the sensor 1, based on the value of the sensed measurement 1 captured by the sensor 2. Similarly, values of other sensed measurements may be collated and weightages may be assigned at blocks 306*b* and 306*c*.

The sensed measurements (M1, M2, M3) may then be provided to a micro-controller (or a processor), at block 308. The micro-controller may determine a value of a health parameter of a user by processing the values of two or more sensed measurements. At block 310, the value of the health parameter may be compared with values of similar health parameters obtained from accurately performing sensors/sensing modules. Based on such comparison, optimum weightages may be determined for one or more of the sensed measurements (M1, M2, M3), and such weightages may be utilized thereafter at block 306 to optimize the values of the sensed measurements (M1, M2, M3).

The preceding description has been presented with reference to various embodiments of the invention. Persons skilled in the art and technology to which this invention pertains will appreciate that alterations and changes in the described structures and methods of operation can be practiced without meaningfully departing from the principle, spirit and scope of this invention.

The invention claimed is:

1. A system for measuring health parameters with context-adaptive sensor fusion, the system comprising:

two or more sensing modules for capturing values of two or more sensed measurements associated with a user;

a memory storing multiple sets of weightages, wherein each set of weightages corresponds to a different context selected from: time of day, user characteristics, presence of motion artifacts, or measurement reliability conditions; and a processor configured to:

(a) determine a current context based on one or more contextual parameters;

(b) select from the memory a set of weightages corresponding to the determined current context;

(c) assign the selected weightages to the values of the two or more sensed measurements; and (d) determine a value of a health parameter using a weighted average of the values with the assigned weightages.

2. The system of claim 1, wherein the different contexts include different times of day, and wherein the processor assigns different weightages for morning measurements compared to evening measurements based on sensor reliability variations throughout the day.

3. The system of claim 1, wherein the processor is configured to:
detect presence of motion artifacts during measurement; and
select a set of weightages that reduces impact of sensing modules susceptible to motion artifacts when motion artifacts are detected.

4. The system of claim 1, wherein the user characteristics include weight management conditions, and wherein the processor selects weightages that prioritize more reliable sensing modules when the user has weight management conditions.

5. The system of claim 1, wherein the system is configured for multi-user operation, and wherein the processor stores context-specific weightages separately for each user of a plurality of users.

6. The system of claim 1, wherein the measurement reliability conditions include determination of signal quality from each sensing module, and wherein the processor dynamically adjusts weightages based on real-time assessment of signal quality during measurement.

7. A system for measuring health parameters with adaptive measurement pathways, the system comprising:
two or more sensing modules;
a memory storing a database comprising:
(a) identification of multiple sets of sensing modules, wherein each set is capable of measuring a same health parameter through different measurement methods; and
(b) accuracy and reliability information for each set of sensing modules;
a processor configured to:
(c) determine availability status of the two or more sensing modules;
(d) identify available sets of sensing modules from the database;
(e) provide to a user options for measuring the health parameter using the available sets along with the accuracy and reliability information; and
(f) capture values and determine the health parameter using a user-selected set of sensing modules.

8. The system of claim 7, wherein the multiple sets of sensing modules include:
a first set comprising an ECG sensing module for measuring heart rate; and
a second set comprising a PPG sensing module for measuring heart rate;
wherein the database stores different accuracy ratings for the first set and the second set.

9. The system of claim 7, wherein the multiple sets of sensing modules for measuring blood pressure include:
a first set comprising a cuff-based oscillometric blood pressure sensing module;
a second set comprising a PPG-based sensing module requiring user-specific calibration; and
a third set comprising a cuff-based blood pressure sensing module synchronized with a digital auscultation sensing module for detecting Korotkoff sounds.

10. The system of claim 7, wherein the processor is further configured to:
notify the user when a preferred set of sensing modules with higher accuracy is unavailable due to a missing sensing module or sub-component; and
recommend attachment of the missing sensing module or sub-component.

11. The system of claim 7, wherein at least one sensing module of the two or more sensing modules includes a detachable sub-component, and wherein the processor is configured to:
detect attachment status of the detachable sub-component; and
update the availability status based on whether the detachable sub-component is attached.

12. The system of claim 7 wherein the processor is further configured to:
determine that a first set of sensing modules requires calibration using a second set of sensing modules before the first set can be used; and
guide the user to perform calibration measurement using the second set before enabling measurement using the first set.

13. A system for measuring health parameters through synchronized sensor operation, the system comprising:
two or more sensing modules for capturing values of two or more sensed measurements associated with a user;
a processor configured to:
(a) determine that measurement of a health parameter requires synchronized operation of the two or more sensing modules;
(b) initiate simultaneous capture of the values by operating the two or more sensing modules in temporal synchronization;
(c) maintain temporal alignment of the captured values; and
(d) determine the health parameter by analyzing timing relationships between the temporally synchronized values.

14. The system of claim 13, wherein:
the two or more sensing modules comprise an ECG sensing module and a PPG sensing module; and
the processor determines pulse arrival time (PAT) or pulse transit time (PTT) by analyzing timing differences between synchronized ECG waveform and PPG waveform measurements.

15. The system of claim 13, wherein:
the two or more sensing modules comprise a cuff-based blood pressure sensing module and a digital auscultation sensing module; and
the processor determines systolic and diastolic blood pressure by synchronizing cuff pressure measurements with detection of Korotkoff sounds from the digital auscultation sensing module.

16. The system of claim 13, wherein the processor is configured to:
detect when the two or more sensing modules have lost temporal synchronization during measurement; and
automatically restart the measurement process when loss of synchronization is detected.

17. The system of claim 13, wherein the processor is configured to derive multiple different health parameters from a single synchronized measurement session, including at least two of: pulse arrival time, pulse transit time, heart rate variability, or blood pressure estimates.

18. A method for measuring health parameters, comprising:

determining, by a processor, availability of two or more sensing modules required to capture values of two or more sensed measurements associated with a user;

capturing, by the two or more sensing modules, the values of the two or more sensed measurements associated with the health of the user; and determining, by the processor, a value of a health parameter by processing the values of the two or more sensed measurements obtained from the two or more sensing modules;

storing, in a memory, user-specific calibration data for a plurality of users wherein the system is configured for multi-user operation; and determining, by the processor, when calibration is required for the user based on one or more of: absence of calibration data for the user, lapse of a predetermined period since last calibration for the user, or deviation of measured values from expected values for the user.

19. The method of claim 18, further comprising:

determining a current context based on one or more of: time of day, user characteristics, or presence of motion artifacts;

selecting a set of weightages from multiple stored sets based on the determined current context;

assigning the selected weightages to the values of the two or more sensed measurements; and determining the value of the health parameter as a weighted average using the assigned weightages.

20. The method of claim 18, wherein determining when calibration is required further comprises:

using an output of a first sensing module of the two or more sensing modules to generate calibration data for a second sensing module of the two or more sensing modules; and storing the calibration data in association with the user in the memory.

* * * * *